United States Patent [19]
Cantor

[11] Patent Number: 6,080,450
[45] Date of Patent: *Jun. 27, 2000

[54] COMPOSITION EXHIBITING IMPROVED FLUORESCENT RESPONSE

[75] Inventor: Stephen E. Cantor, Cheshire, Conn.

[73] Assignee: Dymax Corporation, Torrington, Conn.

[*] Notice: This patent issued on a continued prosecution application filed under 37 CFR 1.53(d), and is subject to the twenty year patent term provisions of 35 U.S.C. 154(a)(2).

[21] Appl. No.: 08/798,169

[22] Filed: Feb. 10, 1997

Related U.S. Application Data

[60] Provisional application No. 60/012,716, Feb. 23, 1996.

[51] Int. Cl.⁷ .................................. C08F 2/50; C08F 4/00; G03C 1/725
[52] U.S. Cl. ............................ 427/517; 427/519; 522/18; 522/28; 522/64; 522/75; 522/96; 522/173; 522/182; 430/281.1; 430/284.1
[58] Field of Search .................................. 522/64, 18, 28, 522/75, 96, 173, 182; 427/517, 519; 430/269, 488.1

[56] References Cited

U.S. PATENT DOCUMENTS

| | | |
|---|---|---|
| 4,298,738 | 11/1981 | Lechtken et al. .......................... 546/22 |
| 4,348,503 | 9/1982 | Bachmann . |
| 4,429,088 | 1/1984 | Bachmann . |
| 4,432,829 | 2/1984 | Bachmann . |
| 4,447,520 | 5/1984 | Henne et al. ............................ 430/281 |
| 4,963,220 | 10/1990 | Bachmann et al. . |
| 4,964,938 | 10/1990 | Bachmann et al. . |
| 5,039,715 | 8/1991 | Bachmann et al. . |
| 5,100,802 | 3/1992 | Mickols .................................... 436/34 |
| 5,162,390 | 11/1992 | Tilley et al. . |
| 5,218,009 | 6/1993 | Rutsch et al. ............................. 522/16 |
| 5,227,240 | 7/1993 | Tilley et al. . |
| 5,302,627 | 4/1994 | Field et al. ............................... 522/13 |
| 5,310,604 | 5/1994 | Melancon et al. ...................... 428/447 |
| 5,559,163 | 9/1996 | Dawsn et al. . |
| 5,660,968 | 8/1997 | Wilczak et al. ......................... 430/253 |
| 5,707,781 | 1/1998 | Wilczak ............................... 430/281.1 |

OTHER PUBLICATIONS

K. Dietliker et al. Proceeding, Rad Tech International, vol. 2., p. 693, 1994.

Primary Examiner—Susan W. Berman
Attorney, Agent, or Firm—Ira S. Dorman

[57] ABSTRACT

The use of a phosphine oxide photoinitiator enables the effective curing of a polymerizable acrylate formulation despite the incorporation of a high concentration of a fluorescing agent, thereby facilitating, and enhancing the efficiency of, evaluation of the cured deposit utilizing its fluorescent response.

15 Claims, 2 Drawing Sheets

COMPOSITION EXHIBITING IMPROVED FLUORESCENT RESPONSE

CROSS-REFERENCE TO PROVISIONAL APPLICATION

This application claims the benefit of Provisional Application Ser. No. 60/012,716, filed Feb. 23, 1996 in the name of Stephen E. Cantor for his invention entitled "Composition Exhibiting Improved Fluorescent Response."

BACKGROUND OF THE INVENTION

The incorporation of fluorescent compounds into coating compositions and the like, to provide a nondestructive method for inspection, has been an area of rapid development in the last decade. (See, for example, U.S. Pat. No. 5,418,855; U.S. Pat. No. 5,310,604; and D. C. Neckers and J. C. Song, *ACS Polymer Material Science*, Eng, 71,69, 1994.) The use of ultraviolet radiation to produce cured coatings and adhesives has also grown in the same period. (See "Chemistry and Technology of UV and EB Formulation for Coatings, Inks and Paints," Vol. 1–5, PKT Oldring Editor; SITA Technology Ltd., London, England, 1991, ISBN 0947798 21 8.)

The prior art describes the incorporation of fluorescing agents into UV-cured conformal coatings as a means for identifying the presence of the cured film and for ensuring that the part has been properly covered with the coatings. (See J. Plardoff, *J. Protect Coatings Linings*, Vol. 9, No. 12, p.7, 1992.) The rapidly increasing industrial use of UV coating has created requirements for on-line, nondestructive measurement, as well as off-line monitoring of cure and depth of cure. Significant emphasis has been directed to the development of optical scanners which can examine documents or packages to which are applied or with which are associated UV cured inks or coatings containing fluorescent compounds, e.g., for detecting counterfeit currency, for bar code identification, etc. Coatings and inks that exhibit increased levels of response to scanner beams serve of course to enhance the effective sensitivity of the scanner, in turn enabling such electro-optical devices to handle more documents at higher speeds and with increased accuracy. It also follows that coatings containing increased levels of fluorescing agents can be reduced in thickness without diminishing the response to irradiation. In addition, the use of thinner coatings will permit excess heat generated by surface mounts or integrated circuits to be dissipated more readily.

Unlike solvent-based lacquers, which require no cure mechanism to form a film, curing of UV-based systems depends upon the correct wavelength of light striking the photoinitiator(s) employed, so as to generate the free radicals by which polymerization of the ingredients (monomers) is effected, and thereby to form the desired polymeric film. In the present state of the art, many of the fluorescing agents that are used for inspection purposes (e.g., substituted oxazole compounds, and fluoranthene), and like applications, absorb radiation in substantially the same region of the spectrum as that in which the photoinitiators employed react to generate the required free radicals. The resultant filtering or blocking phenomenon has limited the concentration of fluorescing agent that can be incorporated into a coating, ink or adhesive formulation, as the case may be, since an excessive amount of the agent will preclude adequate reaction of the ingredients and adequate depth of cure. This factor has in turn impeded the acceptance of UV technology for systems that demand a bright fluorescent response, e.g., for the production of conformal coatings.

More particularly, levels of 0.02 to 0.04 percent of the fluorescing agent can generally be incorporated into compositions containing conventional UV-curing photoinitiators without significant detriment to the depth of cure achieved. When the level of fluorescent material is increased however, such as to improve the brightness of response, it is often found that the coating will not cure properly; thus, even a nominally cured coating of only 1 to 3 mils thickness may have a soft undercoat of wet, uncured material. Exposure to radiation in both the ultraviolet and also the visible spectral regions can have the additional effect of decomposing the fluorescent agent molecule, thereby further diminishing the response of the coating to "black" light irradiation.

Use of photoinitiators which respond to the visible part of the spectrum (i.e. red shift) are one method to obviate the filtering effect of the fluorescing agent. Generally, however, they impart a red or dark yellow color to the resulting film, ink, or adhesive, and hence are undesirable from that standpoint.

The prior art describes the use of mono and bisphosphine oxides as photoinitiators, which can provide excellent depth of cure in titanium oxide-containing UV-curable coatings. The success of these phosphine oxides is attributed to their ability to respond in the near-UV/visible spectral region, and to photo-bleach. (See K. Dietliker et al, *Proceeding*, Rad Tech International, Vol 2., p. 693, (1994)). Certain morpholinophenyl derivatives (e.g., Irgacure 369) and titanium based photoinitiators (e.g., Irgacure 784 DC) are also available, which absorb in the visible region. (Irgacure products are commercially available from the Ciba Geigy Company.)

Acrylate formulations are well known in the art for use as adhesives, potting compounds, conformal coatings, inks, and the like. In addition to including polymerizable acrylate monomers, such formulations typically include elastomeric fillers (e.g., urethane oligomers, preferably capped to provide sites of unsaturation for enhanced reactivity), adhesion promoters in the form of organic acids (e.g., acrylic and methacrylic), inert fillers, supplemental adhesion promoters (e.g., silanes), leveling agents, and other ingredients. Reaction in formulations of this kind is normally initiated by use of a free-radical, active-oxygen catalyst (i.e., a peroxide, a hydroperoxide, or a perester), activated thermally, chemically (e.g., with an amine/aldehyde adduct and transition metal accelerator), aerobically, anaerobically, etc.; they may additionally or alternatively include a photoinitiator that is responsive to actinic radiation.

Illustrative of the prior art that is germane to the acrylate formulations hereinabove referred to are the following Bachmann and Bachmann et al United States patents, all of which are of common assignment herewith to Dymax Corporation of Torrington, Conn.: U.S. Pat. No. 4,348,503, issued Sep. 7, 1982, U.S. Pat. No. 4,429,088, issued Jan. 31, 1984, U.S. Pat. No. 4,432,829, issued Feb. 21, 1984, U.S. Pat. No. 4,963,220, issued Oct. 16, 1990, U.S. Pat. No. 4,974,938, issued Oct. 23, 1990, and U.S. Pat. No. 5,039,715, issued Aug. 13, 1991.

SUMMARY OF THE INVENTION

Accordingly, it is a broad object of the present invention to provide a polymerizable composition that is curable by actinic radiation and that contains a luminescing agent, wherein the luminescing effect can be increased while maintaining or improving the cure properties of the composition.

A more specific object of the invention is to provide such a composition in which the polymerizable ingredient(s)

comprise an acrylate monomer, in which the activating radiation includes the UV spectral region, and in which the luminescent effect is that of fluorescence.

In particular, a primary object of the invention is to provide a UV-curable, polymerizable acrylate composition for use as a coating material (e.g., to produce conformal coatings for printed circuit boards, peelable masks, and the like), as an ink, or as an adhesive, which exhibits good depth of cure despite a substantial content of fluorescing agent(s).

It is also a broad object of the present invention to provide a novel method for the inspection and evaluation of a UV cured deposit of a polymerizable formulation containing a fluorescing agent, the efficacy of which method is increased by the ability to incorporate relatively high levels of the fluorescing agent without detriment to the curing properties of the formulation.

More specific objects are to provide such a method which is capable of effectively evaluating the thickness of the deposited formulation (including void formation), and to provide such a method which is simple and can be carried out on-line, automatically, and as a quality-control measure.

It has now been found that certain of the foregoing and related objects of the invention are attained by the provision of a polymerizable formulation that is curable by ultraviolet radiation, comprising: a free radical-polymerizable liquid composition; a fluorescing agent; and a catalyst system that includes a phosphine oxide photoinitiator component (with or without any other photoinitiator, thermal initiator, or the like catalyst component). The phosphine oxide responds to actinic radiation in the ultraviolet spectral region to generate free radicals, thereby effecting polymerization of the polymerizable liquid composition.

The polymerizable composition will, in most instances, comprise an acrylate monomer, in predominant amount, and the phosphine oxide photoinitiator component will preferably be one that is responsive to a band of radiation that encompasses a range up to at least about 410 nm. The formulation will normally contain at least about 0.02 percent, and most advantageously more than 0.04 percent, of the fluorescing agent, based upon the weight of the formulation. It will normally also contain about 0.15 to 1.0, and preferably about 0.25 to 0.4 percent, of the phosphine oxide photoinitiator component, also based upon the weight of the formulation.

Other objects of the invention are attained by the provision of a method for the evaluation of a cured deposit of a polymerizable formulation, utilizing a polymerizable formulation composed as herein defined. The formulation is deposited upon an object; it is exposed to actinic radiation in the ultraviolet spectral region, to which radiation the phosphine oxide photoinitiator responds for the generation of free radicals, and thereby for the initiation of polymerization of the composition. The polymerized deposit is thereafter irradiated with incident radiation, of a wavelength that is absorbed by the fluorescing agent, to produce a radiant emission.

In certain embodiments the method will include the further step of measuring the energy of the radiant emission, which energy-measuring step is desirably effected using an electro-optical device that is sensitive to at least one wavelength of the radiant emission, and that generates a responsive electrical signal that is indicative of the energy measured in the measuring step. More particularly, the method may be employed to evaluate the thickness of the cured deposit, with the incident radiation being of controlled (e.g., constant) intensity and being projected as a beam of controlled transaxial area. The depositing, exposing, irradiating, and measuring steps may be carried out on a polymerized deposit present on each of a multiplicity of objects, with the beam of incident radiation irradiating substantially the same area of each deposit and with the method including the further steps of comparing each of the generated indicative signal with a preselected standard, and of generating a control signal based upon each comparison.

DETAILED DESCRIPTION OF THE PREFERRED AND ILLUSTRATED EMBODIMENTS

Figure 1:
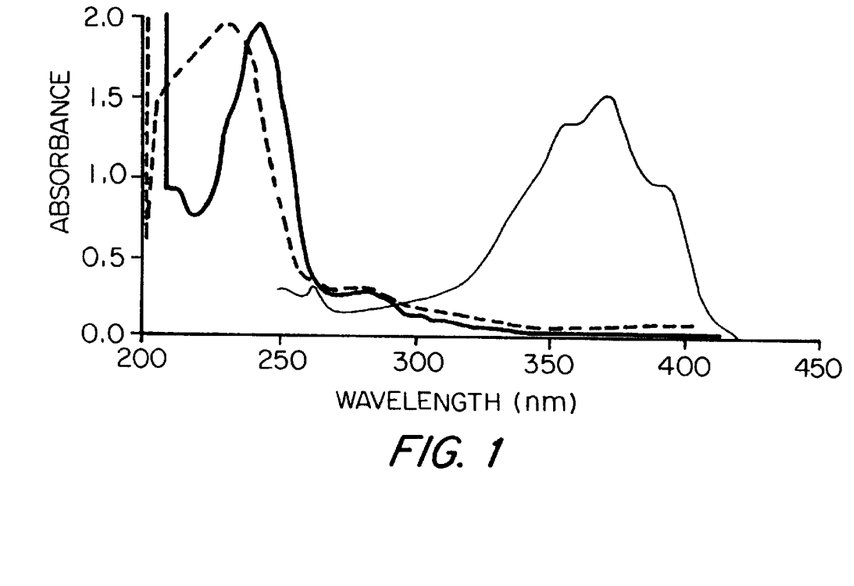
FIG. 1 is a plot of absorbance as a function of wavelength for each of three compounds.

In FIG. 1, (1) the thin line represents the response of the oxazole fluorescing agent sold by Angstrom Technology, Erlanger, Ky., under the trade designation "Scanning Compound #5"; (2) the thick line represents the response of the photoinitiator bis (2,6-dimethoxybenzoyl)-2,4,4-trimethylpentyl phosphine oxide (DMBAPO), the product being sold by Ciba Geigy Company, under the designation Irgacure CGI 1700, as a 25% solution of the phosphine oxide in the conventional Darocure 1173 photoinitiator; and (3) the dotted line represents the response of the photoinitiator 2,4,5-trimethyl benzoyl diphenylphosphine oxide (TPO), the product being sold by Ciba Geigy Company, under the designation Darocure 4265, as a 50% solution of the phosphine oxide in Darocure 1173.

The phosphine oxide photoinitiators (e.g., Irgacure CGI 1700 and Darocure 4265) and certain "red shift" photoinitiators effect curing upon exposure to UV and visible light, but are unaffected by the filtering effect of the fluorescing agents. This is a surprising result because the UV absorbance spectrum of the fluorescing agents resides in the part of the spectrum (i.e., 310 nm to 385 nm) in which the phosphine oxide photoinitiators generally absorb. FIG. 1 clearly expresses this relationship. It is noted that the critical absorbance region of the phosphine oxides, regarded to be from 340 nm to 390 nm, and most critically at 365 nm, is the very region in which the oxazole fluorescing agent absorbs, as a result of which one would expect either no response, or at best, a limited response to the initiating UV source. Such a filtering effect is produced, for example, by the standard benzoin, benzilketals, α,α-dialkoxyacetopheones, α-hydroxalkylphenones and α-aminoalkylphenone Type I photoinitiators, as well as by the Type II photoinitiators such as benzophenone/amine and thixoanthone. As will be described more fully hereinbelow, the phosphine oxide photoinitiators provide outstanding cure through volume in formulations in which the fluorescing agent is incorporated at levels (i.e., 0.1% to 0.5%) that are significantly increased over standard concentrations, and yet produce clear, non-discolored products.

Thus, the present invention provides a method for enhancing the fluorescent response to long wavelength ultraviolet radiation ("black" light). Coatings, inks, or adhesives can be prepared with significant quantities of fluorescing agents, so that detection of the fluorescent energy that is emitted upon suitable irradiation can either be achieved directly, by the human eye, or in an automatic mode by an on-line electro-optical device. In addition to being useful for anti-counterfeiting, as discussed above, such electro-optical instruments can be employed in a highly effective manner to measure coating thickness and completeness of cure in the instant formulations.

Exemplary of the efficacy of the present invention are the specific examples set forth below. The functional coating compositions employed in these examples comprise an end-capped polyurethane oligomer acrylate, acrylate monomer(s), flow agents, anti-oxidants (for stability), photoinitiator(s), and leveling agents.

In certain cases, dyes and UV-stable pigments are also included to form UV curable ink products, in contrast (for example) to clear conformal coatings. Thickeners and fillers can be added to produce thixotropic adhesives useful for peelable masks.

The following conventional photoinitiators may for example be employed: 1-hydroxyl cyclohexyl phenyl ketone (Irgacure 184); dimethoxy-2-phenylacetophenone (Irgacure 651); 2-benzyl-2-N,N-dimethyl amino-1-(4-morpholinophenyl)-1-butanone (Irgacure 369); Bis($u^5$-2,4-cycloypentadien-1-yl) bis[2,6-difluoro-3-(1H-pyrrol-1-yl) phenyl]titanium (Irgacure 784DC); and 2-hydroxy-2-methyl-1-phenyl-propan-1-one (Darocure 1173). The fluorescing compounds evaluated are: (1) a proprietary substituted oxazole compound sold by and Angstrom Technologies and designated "Scanning Compound #5"; (2) fluoranthene (Aldrich Chemical Company); and (3) 2,2'-(2,5-thiophenediyl)bis[5-tert butyl benzoxazole], sold by Ciba Geigy Company under the trade designation "Uvitex OB." The foregoing compounds fluoresce or phosphoresce at wavelengths above 350 nm, and particularly in the visible range (400 nm to 700 nm) when stimulated by exposure to long wavelength UV "black" light. Such compounds are commonly aromatic in character, they may or may not be substituted, and they may or may not be hetrocyclic.

In the examples that follow, amounts of ingredients are expressed in parts by weight, and cure depths are expressed in millimeters:

EXAMPLE ONE

The indicated ingredients are admixed to provide a formulation that is functional as a conformal coating:

| FORMULATION A | |
|---|---|
| Polyurethane-acrylate oligomer | 45.0 |
| Isobornyl acrylate | 47.0 |
| Acrylic acid | 4.2 |
| Tert-butyl perbenzoate | 2.4 |
| Irganox MD 1024 (stabilizer) | 0.1 |
| Photoinitiator (Irgacure 184) | 2.0 |

Table I below describes experiments using compositions in which the level of fluorescing agent (Scanning Compound #5) was varied as the level of a phosphine oxide photoinitiator (CGI 1700) remained constant, when included. Depth of cure was measured by pouring the test composition into a plastic bulb, which was in turn placed in a cavity formed in a black rubber stopper. After exposure to UV light (a Fusion Lamp, rated at 7.8 joules/cm$^2$), the depth of the resulting cured plug was measured.

TABLE I

| | 1 | 1-A | 2 | 2-A | 3 | 3-A |
|---|---|---|---|---|---|---|
| Formulation A | 98 | 98 | 98 | 98 | 98 | 98 |
| Scanning Compound #5 | 0.02 | 0.02 | 0.10 | 0.10 | 0.45 | 0.45 |
| CGI 1700 | — | 1.0 | — | 1.0 | — | 1.0 |
| Depth of Cure | 7.0 | 35.0 | 1.0* | 15.0 | 1.0* | 20.0 |
| Response to "black" light | F | F | VB | VB | VB | VB |

*Only surface cure; wet and soft below the surface.
F = faded and dull
VB = very bright These data demonstrate that only at a low concentration (0.02 percent) of Scanning Compound #5 (experiment 1) can a depth of cure of 7 mm be obtained in the absence of the phosphine oxide photoinitiator, and that the resulting coating displays only a moderate degree of response upon exposure to "black" light.

Experiments 2 and 3, in which the level of Scanning Compound #5 is increased five fold and 22.5 fold, respectively, fail to provide any significant depth of cure. When one part of the phosphine oxide compound is included, however (experiments 1-A, 2-A and 3-A), very substantial depth of cure and very bright response is observed in all instances.

It has been found that the incorporation of five parts of Darocure 1173 photoinitiator (the liquid carrier for the two commercial phosphine oxides) into the experiment 3 composition fails to provide a depth of cure in excess of 2 mm; i.e., the extra amount of photoinitiator does not improve the result. Thus, only the formulations in which the phosphine oxides are present display enhanced fluorescent response while maintaining excellent depth of cure.

EXAMPLE TWO

Darocure 4265 phosphine oxide photoinitiator was used in place of CGI 1700 in the 1-A and 2-A compositions of Example One. Cure depth under the operating conditions described was 12 mm (1-A) and 9 mm (2-A), respectively, and each formulation exhibited an excellent response to "black" light. Here again, in the absence of the Darocure 4265 initiator only a surface cure was noted.

EXAMPLE THREE

Formulation A of Example One was used to examine the effect of the fluoranthene fluorescing agent, using a constant amount of CGI 1700. Cure was effected by exposure for 30 seconds to an EC-5000 lamp (available from Dymax Corporation, of Torrington, Connecticut) having an intensity of 200 milliwatts/cm$^2$. The results are reported in Table II below:

TABLE II

|  | 1 | 1-A | 2 | 2-A | 3 | 3-A | 4 | 4-A | 5 | 5-A |
|---|---|---|---|---|---|---|---|---|---|---|
| Formulation A | 98 | 98 | 98 | 98 | 98 | 98 | 98 | 98 | 98 | 98 |
| Fluoranthene | 1.0 | 1.0 | 0.5 | 0.5 | 0.25 | 0.25 | 0.125 | 0.125 | .062 | .062 |
| CGI 1700 | 1.5 | -0- | 1.5 | -0- | 1.5 | -0- | 1.5 | -0- | 1.5 | -0- |
| Depth of cure | 18.0 | 1.0 | 20.0 | 1.0 | 30.0 | 3.0 | 32.0 | 6.0 | 29.0 | 6.0 |
| Response to black light | B | B | B | B- | B | B- | B- | D | D | D |

B = Bright
B- = Less than bright
D = Dull

Here again, only in experiments 1, 2, and 3 (in which the level of fluoranthene is relatively high) is there a good response to black light inspection. Also, the depth of cure is unsatisfactory in all instances until the CGI-1700 is incorporated, as is demonstrated by comparison of experiments 1 and 1A, 2 and 2A, and 3 and 3A, respectively.

EXAMPLE FOUR

Formulation A was used to examine the effect of the Uvitex OB fluorescing agent under the same cure conditions as were employed in Example One. Table III below presents the data and results, from which it can be seen that satisfactory depth of cure is achieved only when the phosphine oxide photoinitiator was included:

TABLE III

|  | 1-A | 1 | 2-A | 2 | 3-A | 3 |
|---|---|---|---|---|---|---|
| Formulation A | 99.0 | 99.0 | 99.0 | 99.0 | 99.0 | 99.0 |
| Uvitex OB | 1.0 | 1.0 | 0.5 | 0.5 | 0.25 | 0.25 |
| CGI 1700 | 1.5 | -0- | 1.5 | -0- | 1.5 | -0- |
| Depth of cure | 9.0 | 1.0 | 13.0 | 1.5 | 19.0 | 1.5 |
| Response to black light | B | B | B | B | B | B |

EXAMPLE FIVE

Table IV below sets forth data obtained by employing two other "red" shift photoinitiators in Formulation A with each of the three fluorescing agents employed in Examples One through Four. In all instances 98.5 parts of Formulation A are employed, and the compositions cure through depth and respond to black light; the products of experiments 1, 2 and 3 are quite yellow; those of experiments 4, 5 and 6 are dark red, and those of experiments 7, 8 and 9 have a very light shade of coloration.

TABLE IV

|  | 1 | 2 | 3 | 4 | 5 | 6 | 7 | 8 | 9 |
|---|---|---|---|---|---|---|---|---|---|
| Formulation A | 98.5 | < | < | < | < | < | < | < | < |
| Uvitex OB | 0.5 | — | — | 0.5 | — | — | 0.5 | — | — |
| Scanning Compound #5 | — | 0.5 | — | — | 0.5 | — | — | 0.5 | — |
| Fluoranthene | — | — | 0.5 | — | — | 0.5 | — | — | 0.5 |
| Irgacure 369 | 1.0 | 1.0 | 1.0 | — | — | — | — | — | — |
| Irgacure 784 | — | — | — | 1.0 | 1.0 | 1.0 | — | — | — |
| CGI 1700 | — | — | — | — | — | — | 1.0 | 1.0 | 1.0 |

EXAMPLE SIX

The indicated ingredients are admixed to provide a formulation that is functional as a peelable mask coating (i.e., a flexible conformal coating):

| Formulation B | |
|---|---|
| Polyester polyurethane oligomer | 64.0 |
| N,N-dimethyl acrylamide | 20.0 |
| High boiling acrylate monomer | 9.0 |
| CGI 1700 | 1.85 |
| Inorganic filler | 2.3 |
| Irganox MD 1024 | 0.1 |
| Scanning Compound #5 | 0.05 |

The formulation has a viscosity of 34,000 cps; it cures to a Shore A hardness value of 75 in 10 seconds. A ⅛ inch bead of the material was fully reacted in 10 seconds under exposure to a 200 milliwatts/cm$^2$ UV source; it cures throughout its entire volume, and displays a bright fluorescence under black light.

EXAMPLE SEVEN

The following formulation functions as a fluorescing, UV-curing ink.

| Polyurethane acrylate oligomer | 32 |
|---|---|
| Isobornylacrylate | 43 |
| Hexanediol diacrylate | 4.2 |
| Photoinitiator (Irgacure 651) | 2.0 |
| TPO (phosphine oxide) | 1.0 |
| High boiling acrylate monomer | 13 |
| Inorganic filler | 4.8 |
| Scanning Compound #5 | 0.1 |
| Penn color blue | 0.03 |

The ink, when cured, displays a blue color and fluoresces under "black" light.

EXAMPLE EIGHT

Table V below describes experiments in which the level of fluorescing agent was varied in compositions employing Formulation B (defined above) as the level of the CGI 1700 was kept constant. These data demonstrate that the phosphine oxide initiator does not adversely affect the brightness level.

TABLE V

|  | 1 | 2 | 3 | 4 | 5 | 6 |
|---|---|---|---|---|---|---|
| Formulation B | 99.9 | 98.9 | 99.9 | 98.8 | 99.5 | 98.5 |
| CGI 1700 | — | 1.0 | — | 1.0 | — | 1.0 |
| Scanning Compound #5 | 0.02 | 0.02 | 0.1 | 0.1 | 0.5 | 0.5 |
| Depth of cure | 2.0 | 22.0 | 2.0 | 14.0 | 0 | 9.0 |
| Appearance under black light | D | D | B | B | VB | VB |

EXAMPLE NINE

Formulation B was used to prepare a composition containing two fluorescing compounds. In this instance, curing was effected by exposing the compositions to a Fusion Lamp (rated at about 2000 milliwatts per square centimeter), spaced four inches away from deposits on a conveyor moving at 1.2 feet per minute. The results, expressed in Table VI, demonstrate that the benefits of the invention can be realized using blends of fluorescing agents, as may afford economic advantages.

TABLE VI

| Formulation B | 98.0 |
|---|---|
| CGI 1700 | 1.0 |
| Scanning Compound #5 | .02 |
| Uvitex OB | 1.0 |
| Depth of cure | 10.0 |
| Appearance under black light | B |

Although the phosphine oxides are usually used in combination with conventional photoinitiators, that is done primarily as a matter of convenience. The phosphine oxide photoinitiators employed are solid compounds, and the secondary photoinitiators serve readily to provide them in a liquid form. Needless to say, another ingredient of the formulation (e.g., a reactive monomer) could be employed as a vehicle for introducing the phosphine oxide compound, as the sole catalyst component, if so desired. The following Example demonstrates that the phosphine oxide photoinitiators function in a highly advantageous manner, in the absence of other photoinitiators.

EXAMPLE TEN

A formulation was prepared to contain the same ingredients as Formulation A, with the exception that the Irgacure 184 was omitted, and 0.6 part of TPO was introduced, per se, in admixture with the oligomer and acrylate monomer ingredients. The resulting formulation, and the same formulation modified by the introduction of 0.1 part of Scanning Compound #5 (a relatively high concentration), were tested for depth of cure, in the manner described in Example One. A cure depth of 15 mm was obtained in the unmodified formulation, whereas the formulation containing the fluorescing agent cured to a depth of 8 mm; in both instances, a very bright response to black light irradiation was observed.

Figure 2:
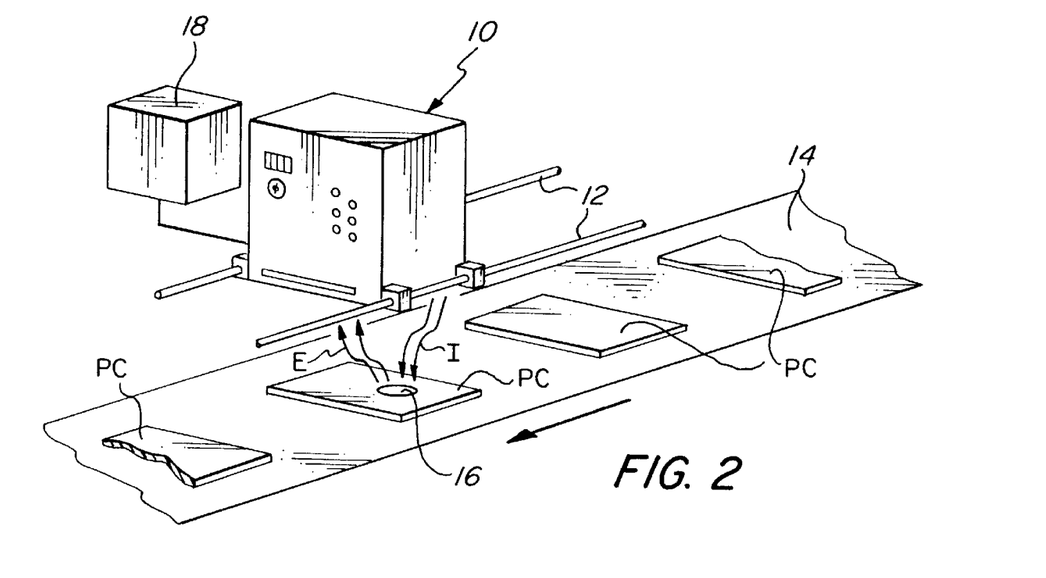
FIG. 2 is a schematic representation of a system for evaluating the deposits produced upon a set of printed circuit boards.

The system of FIG. 2 is suitable for use in carrying out a non-contact method for evaluating the thickness of a cured deposit. Such a technique is especially valuable in situations in which the deposit is thin relative to the substrate (e.g., where the deposit is a conformal coating on a printed circuit board), which condition renders it most difficult to measure thickness accurately. The system consists of an electro-optical scanner, generally designated by the numeral 10 (e.g., the instrument identified as Model 2000 H, which is commercially available from Angstrom Technologies, Inc.) mounted upon parallel supporting rods 12 above an array of coated printed circuit boards "PC," transported upon a conveyor 14. The scanner 10 generates an incident black light beam "I," focussed to impinge upon each board PC as a spot 16 of constant area, and incorporates electro-optical means for detecting radiation "E" emitted from the spot 16, and for producing an electric current signal having a voltage (typically of millivolt magnitude) that is representative of the energy of the detected radiation E, and hence of the thickness of the deposit (the quantity of fluorescent light being proportional to three factors, namely, the intensity of the incident radiation, the area irradiated, and the coating thickness). The signals that are generated as the coated boards PC are conveyed under the scanner 10 (or as the scanner is translated over the boards) may be used directly for manual, semi-automatic, or fully automatic control purposes (e.g., to indicate that a given workpiece PC is of either acceptable or unacceptable quality, based upon a preestablished criterion, and to actuate a rejection mechanism if the criteria are not reached or are exceeded), and/or it may be impressed upon electronic data processing means 18 for the foregoing purpose or for any of numerous other purposes, e.g., to generate a record such as the bar chart of FIG. 3.

Figure 3:
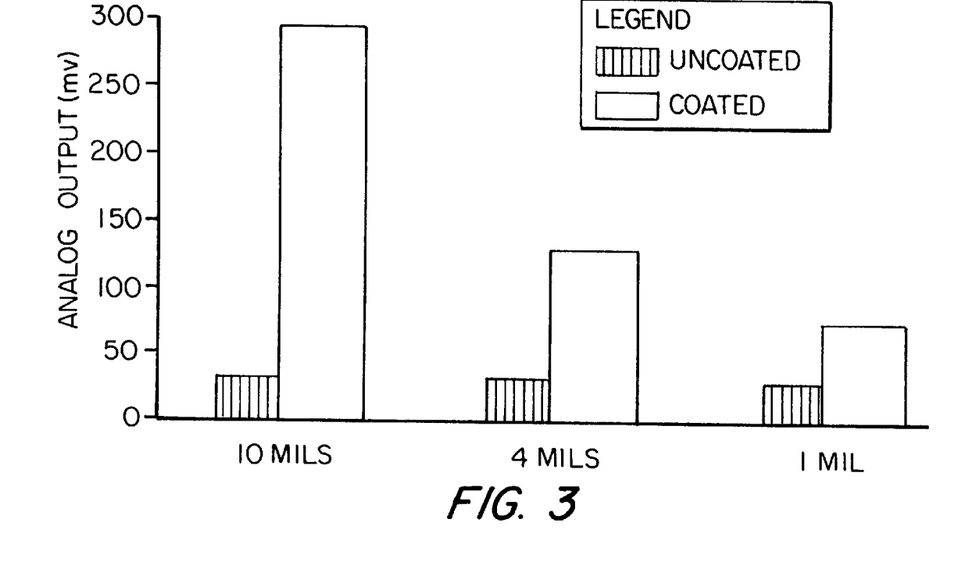
FIG. 3 is a bar chart showing data that are indicative of coating thickness evaluations obtained using the system of FIG. 2.

More particularly, the data of FIG. 3 were obtained by preparing several sets of FR-4 boards, carefully coated with Formulation A of Example One, using very accurate draw-down bars to produce deposits 1, 4 and 10 mils thick, which were then cured using UV light in the manner described. The coated boards were evaluated using the system of FIG. 2, together with uncoated FR-4 boards which served as controls and also represented void regions. It will be noted that the values obtained for the three coating thickness are not directly proportionate (i.e., they do not bear a linear relationship to one another); they are however sufficiently distinct to enable them to serve as criteria for a pass or fail quality control inspection scheme. It will also be noted that the 35 millivolt reading can be taken as the background value.

A system similar to that of FIG. 2 (but employing the Angstrom Technologies Model 3000 MR instrument) was used for the inspection of anesthesia masks, i.e., to detect the presence of impermissible voids in the line of adhesive that is used to bond the polyvinyl pillow to the rigid cowling of which such masks are constructed. The adhesive employed was a formulation embodying the present invention, cured by exposure to an appropriate dose of UV radiation. Utilizing a black-light source placed inside the mask assembly, and scanning the bond line from the outside, the computer-generated trace of FIG. 4 was produced, the numerical values indicated being the millivolt readings detected by the instrument.

Figure 4:
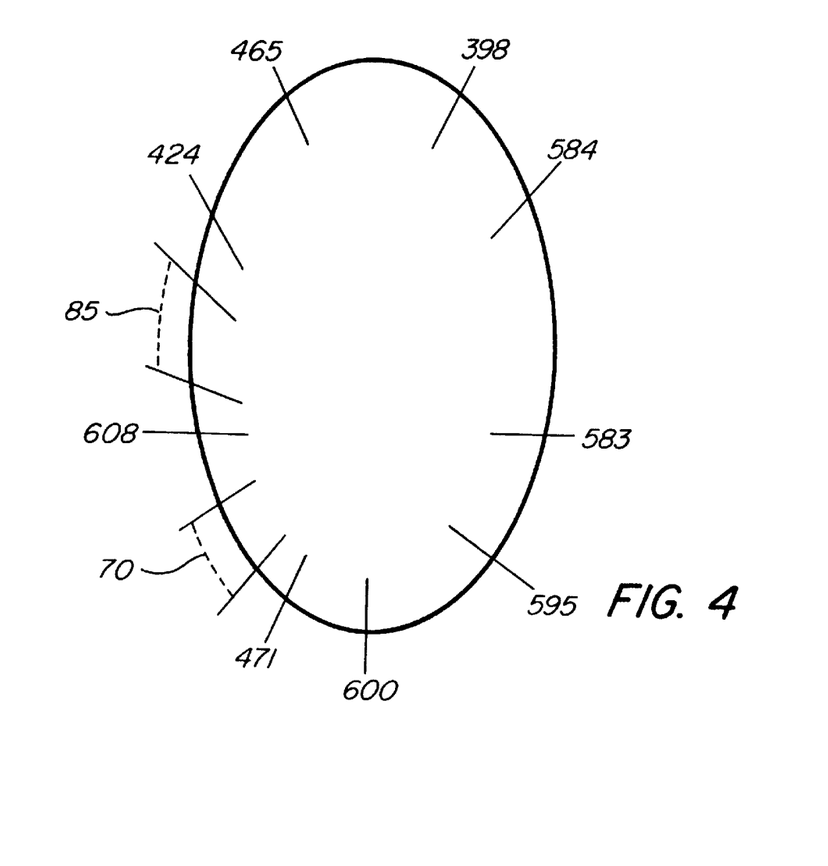
FIG. 4 is a graphic representation of a bond line for an anesthesia mask, showing fluorescent emission readings taken at 11 points about is periphery.

Adhesive was intentionally omitted from two sections of the cowling/pillow joint, as is confirmed by the 70 and 85 millivolt readings recorded. Such automatic reading and graphic representation is an important attribute, because it enables the production of a direct permanent record of the quality control evaluation that was performed in connection with each mask, as may be germane to any official audit (e.g., of medical devices by the U.S. Food and Drug Administration). Nevertheless, it is to be appreciated that the enhanced fluorescent response afforded by the instant formulations is sufficiently pronounced as to enable evaluation under ambient lighting conditions, thus obviating any need for off-line handling to confirm adherence to required bonding specifications.

A variety of formulations suitable for use in the practice of the present invention will be evident, from the present description, to those skilled in the art. As pointed out above however, acrylate compositions such as those described in the above-identified Bachmann and Bachmann et al patents are regarded to be preferred. It might therefore be particularly pointed out that reactive acrylate monomers suitable for use in the such formulations include both monofunctional and polyfunctional acrylates and methacrylates. They will generally be reaction products of acrylic acid and/or methacrylic acid with one or more mono- or poly-basic, substituted or unsubstituted, alkyl ($C_1$ to $C_{18}$), aryl or aralkyl alcohols. Acrylates in which the alcohol moiety contains a polar substituent (e.g., anhydroxyl, amine, halogen, cyano, heterocyclic or cyclohexyl group) will often be preferred because crosslinking, or other intermolecular bonding, is promoted thereby. Suitable such monomers are well known in the art, and are in part disclosed for example at line 53, column 6, through line 35, column 7 of Bachmann et al patent No. 4,429,088, and at line 14, column 4 through line 52, column 5 of patent No. 4,451,523. Nevertheless, it might be noted that the following acrylates and corresponding methacrylates (the methacrylate compounds being preferred in many instances) are especially suitable for use in the present compositions, alone or in combination with one another: hydroxyethylacrylate, isobornyl acrylate, tetrahydrofurfuryl acrylate, diethyleneglycol diacrylate, 1,4-butanediol diacrylate, butylene glycol-diacrylate, neopentyl glycol diacrylate, octylacrylate and decylacrylate (normally in admixture), polyethyleneglycol diacrylate, trimethylcyclohexyl acrylate, benzyl acrylate, butyleneglycol diacrylate, polybutyleneglycol diacrylate, tripropyleneglycol diacrylate, trimethylolpropane triacrylate, di-trimethylolpropane tetraacrylate, pentaerythritol tetraacrylate, and di-pentaerythritol pentaacrylate.

About 1 to 10 weight percent of acrylic acid or methacrylic acid will beneficially be employed, to increase adhesion. A tautomeric acid constituent may also contribute to bond strength; although maleic acid is preferred, other acids capable of cyclic tautomerism can also be used, such as malic, salicylic, itaconic and phthalic.

A free-radical reactive oligomer will normally be included in such acrylate compositions, alone or, where appropriate, in combination with a cationic-reactive oligomer. Oligomers suitable for use are also well known in the art, and comprise vinyl polymers, acrylic polymers, polyester elastomers, glycol polymers, acrylated epoxies, natural and synthetic rubbers, polyester acrylates, epoxy acrylates, polyether acrylates, alkyd acrylates, polyol acrylates, and the like. However, the use of the urethane polymers and prepolymers will often be found most beneficial, with the latter being especially desirable due to the potential that they afford for further reaction of their pendant isocyanate groups with a reactive functionality (e.g., an hydroxyl group) provided by a suitable acrylate monomer. Diisocyanate-capped polyethers and polyesters, acrylated by reaction with hydroxyethyl acrylate or hydroxyethyl methacrylate and having a molecular weight of about 400 to 6,000, are particularly preferred.

Acrylate compositions may also include a vinyl ether reactive diluent, such as those that conform to the structural formula:

in which formula each of the substituents R, R' and R" independently represents an hydrogen atom, an aliphatic group, or an aromatic group; n is an integer, usually having a value from 1 to 6; and Q represents an aliphatic group, an aromatic group, an alkoxy group, a cycloaliphatic group, an ester group, a polyester group, an ether group, a polyether group, a carbamide group, a carbamate group, an heterocyclic group, or the like, each of such groups optionally being further substituted by an hydroxyl or a vinyl group, or both. Vinyl ether-terminated ester monomers and vinyl ether-terminated aromatic urethane oligomers may find utility herein, and it is believed that analogous compounds in which a sulfur atom replaces the oxygen of the ether group(s) may be used as well (alone or in combination) as a diluent ingredient.

In addition to the compounds identified above, a further listing of conventional photoinitiators may be obtained by reference to U.S. Pat. No. 4,820,744, particularly at line 43, column 4, through line 7, column 7. It is believed that cationic photoinitiators may also be employed, to provide a further cure mechanism in appropriate circumstances.

Particularly in instances in which the formulation is to be used as a potting compound, it may be especially desirable to incorporate a chain transfer agent of the kind that is typically used in compositions cured by electron beam initiation; e.g., halogen compounds, sulfur compounds, and secondary and tertiary aromatic hydrocarbons such as cumeme, carbon tetrachloride, 1,4-disopropyl benzene, t-butyl benzene, bisphenol A and glycidyl ether derivatives thereof, etc. The use of chain transfer agents may serve to increase the Shore D hardness of the resultant polymer, the degree of which will depend to an extent upon the concentration of the agent in the formulation, which typically will be 0.5 to 5.0, and usually 0.1 to 1.0, weight percent.

Other materials may be incorporated into the instant compositions in addition to the components hereinabove described. For example, "inert" fillers such as wood flour, cornstarch, glass fibers, cotton linters, mica, alumina, silica, and the like, may be used to modify viscosity, improve impact resistance, and for other purposes, and it is conventional to include small percentages of silane coupling agents to increase moisture resistance as well as to enhance bond strength to glass and similar surfaces. Substances such as dyes, flame retarders, stabilizers (e.g., the quinones and hydroquinones), viscosity modifiers (thixotropes, thickeners, viscosity reducers), plasticizers, antioxidants, and the like, may be incorporated as well.

The composition will often be provided as two or more components that are so composed as to produce, in combination, the desired final properties of the cured deposit, coupled with satisfactory shelf-life and pot-life of the individual and mixed components, good rheological and flow characteristics, and other necessary or desirable properties. Although the composition will normally be free from non-reactive solvents, it will be appreciated that small amounts of water and/or other solvents may necessarily be present as a practical matter, such as to facilitate the introduction of an ingredient. It will often be convenient to use a two-component formulation in a 1:1 volumetric ratio, especially in those instances in which automatic application is to be employed, and the components will be formulated accordingly; other ratios may of course be preferred in given instances, and of course the formulation may be supplied as a multi-part composition if so desired.

Thus, it can be seen that the present invention provides a polymerizable composition that is curable by actinic radiation and that contains a luminescing agent, wherein the luminescing effect is increased while maintaining or improving the cure properties of the composition. More specifically, the polymerizable ingredient(s) will advantageously comprise an acrylate monomer, the activating radiation will normally include the UV spectral region, and the luminescent effect will usually be that of fluorescence. In particular, the invention provides a UV-curable, polymerizable acrylate composition for use as a coating material, as an ink, or as an adhesive, which composition exhibits good depth of cure despite a substantial content of fluorescing agent(s).

The invention also provides a novel method for the inspection and evaluation of a UV cured deposit of a polymerizable formulation containing a fluorescing agent, the efficacy of which method is increased by the ability to incorporate relatively high levels of the fluorescing agent without detriment to the curing properties of the formulation. The method of the invention is capable of effectively evaluating the thickness of the deposited formulation (including void formation); it is simple to perform, and can be carried out on-line, automatically, and as a quality-control measure if so desired.

Having thus described the invention, what is claimed is:

1. A polymerizable liquid formulation that is curable by a combination of ultraviolet and visible radiation to a fully cured solid deposit that exhibits a bright fluorescent response, comprising: a free radical-polymerizable liquid composition; about 0.02 to 1.0 percent of a fluorescing agent, based upon the weight of said formulation, said fluorescing agent fluorescing at wavelengths above 350 nm and including at least a portion of the visible region of the spectrum; and a catalyst system including 0.15 to 1.0 percent, based upon the weight of said formulation, of a phosphine oxide photoinitiator component that responds to actinic radiation in a band of radiation that encompasses a range up to at least 410 nm and that includes at least a portion of the visible spectral region and at least a portion of the ultraviolet spectral region, to generate free radicals and to thereby effect polymerization of said polymerizable liquid composition, said formulation being substantially free of non-reactive solvents.

2. The formulation of claim 1 wherein said composition comprises an acrylate monomer in predominant amount.

3. The formulation of claim 1 containing more than 0.04 percent of said fluorescing agent, based upon the weight of said formulation.

4. The formulation of claim wherein said formulation contains about 0.25 to 0.4 percent of said phosphine oxide photoinitiator component, based upon the weight of said formulation.

5. The formulation of claim 1 wherein said fluorescing agent is a compound selected from the group consisting of substituted oxazole compounds and fluoranthene.

6. A polymerizable liquid formulation that is curable by a combination of ultraviolet and visible radiation to a fully cured solid deposit that exhibits a bright fluorescent response, consisting essentially of: a free radical-polymerizable liquid composition consisting essentially of a reactive acrylate monomer, a free radial reactive oligomer, an organic acid adhesion promotor, and a reactive diluent as an optional ingredient; about 0.02 to 1.0 percent of a fluorescing agent, based upon the weight of said formulation, said fluorescing agent fluorescing at wavelengths above 350 nm and including at least a portion of the visible region of the spectrum; and a catalyst system including 0.15 to 1.0 percent, based upon the weight of said formulation, of a phosphine oxide photoinitiator component that responds to actinic radiation in a band of radiation that encompasses a range up to at least 410 nm and that includes at least a portion of the visible spectral region and at least a portion of the ultraviolet spectral region, to generate free radicals and to thereby effect polymerization of said polymerizable liquid composition; said formulation being substantially free of non-reactive solvents.

7. A method for the evaluation of a cured deposit of a polymerizable formulation, comprising the steps:

providing a polymerizable liquid formulation that is curable by a combination of ultraviolet and visible radiation to a fully cured deposit that exhibits a bright fluorescent response, comprising: a free radical-polymerizable liquid composition; about 0.02 to 1.0 percent of a fluorescing agent, based upon the weight of said formulation, said fluorescing agent fluorescing at wavelengths above 350 nm and including at least a portion of the visible region of the spectrum; and a catalyst system including 0.15 to 1.0 percent. based upon the weight of said formulation, of a phosphine oxide photoinitiator component that responds to actinic radiation in a band of radiation that encompasses a range up to at least 410 nm and that includes at least a portion of the visible spectral region and at least a portion of the ultraviolet spectral region, to generate free radicals and to thereby effect polymerization of said polymerizable liquid composition, said formulation being substantially free of non-reactive solvents;

providing an object;

depositing said formulation upon said object;

exposing said deposited formulation to actinic radiation in said range encompassed by said band to which said phosphine oxide photoinitiator responds for the generation of free radicals, to thereby initiate polymerization of said composition; and irradiating the polymerized deposit with incident radiation of a wavelength that is absorbed by said fluorescing agent to produce a radiant emission.

8. The method of claim 7 including the further step of measuring the energy of said radiant emission.

9. The method of claim 8 wherein said energy-measuring step is effected using an electro-optical device that is sensitive to at least one wavelength of said radiant emission and that generates a responsive electrical signal that is indicative of the energy measured in said measuring step.

10. The method of claim 9 wherein the thickness of said cured deposit is evaluated, said incident radiation being of controlled intensity and being projected as a beam of controlled transaxial area.

11. The method of claim 10 wherein said incident radiation is maintained at a substantially constant intensity.

12. The method of claim 11 wherein a multiplicity of said objects are provided, wherein said formulation is deposited upon each of said objects, and wherein said exposing, irradiating, and measuring steps are carried out on said deposit on each of said objects, said beam of incident radiation irradiating substantially the same area of said each polymerized deposit during said irradiating step, and said method including the further steps of comparing each of said generated indicative signals with a preselected standard, and of generating a control signal based upon each comparison.

13. The method of claim 7 wherein said composition comprises an acrylate monomer in predominant amount; and wherein said fluorescing agent is a compound selected from the group consisting of substituted oxazole compounds and fluoranthene.

14. The method of claim 13 wherein the percentage of said photoinitiator is about 0.25 to 0.4, and wherein the percentage of said fluorescing agent is more than 0.04.

15. A method for the evaluation of a cured deposit of a polymerizable formulation, comprising the steps:

providing a polymerizable liquid formulation that is curable by a combination of ultraviolet and visible radiation to a fully cured solid deposit that exhibits a bright fluorescent response, consisting essentially of: a free radical-polymerizable liquid composition consisting essentially of a reactive acrylate monomer, a free radical reactive oligomer, an organic acid adhesion promotor, and a reactive diluent as an optional ingredient; about 0.02 to 1.0 percent of a fluorescing agent, based upon the weight of said formulation, said fluorescing agent fluorescing at wavelengths above 350 nm and including at least a portion of the visible region of the spectrum; and a catalyst system including 0.15 to 1.0 percent, based upon the weight of said formulation, of a phosphine oxide photoinitiator component that responds to actinic radiation in a band of radiation that encompasses a range up to at least 410 nm and that includes at least a portion of the visible spectral region and at least a portion of the ultraviolet spectral region, to generate free radicals and to thereby effect polymerization of said polymerizable liquid composition, said formulation being substantially free of non-reactive solvents;

providing an object;

depositing said formulation upon said object;

exposing said deposited formulation to actinic radiation in said range encompassed by said band to which said phosphine oxide photoinitiator responds for the generation of free radicals, to thereby initiate polymerization of said composition; and irradiating the polymerized deposit with incident radiation of a wavelength that is absorbed by said fluorescing agent to produce a radiant emission.

* * * * *